United States Patent [19]

Koprowski et al.

[11] Patent Number: 5,053,224
[45] Date of Patent: Oct. 1, 1991

[54] INDUCTION OF ANTIBODY RESPONSE TO SOLID TUMORS WITH ANTI-IDIOTYPE ANTIBODIES

[76] Inventors: Hilary Koprowski, 334 Fairhill Rd.; Dorothee Herlyn, 1223 Knox Rd., both of Wynnewood, Pa. 19096; Elaine C. DeFreitas, 731 Newtown Rd., Villanova, Pa. 19085

[21] Appl. No.: 89,574

[22] Filed: Aug. 26, 1987

Related U.S. Application Data

[63] Continuation of Ser. No. 549,505, Nov. 7, 1983, abandoned.

[51] Int. Cl.$^5$ .................... A61K 39/395; C07K 15/28
[52] U.S. Cl. ..................... 424/85.8; 530/387; 530/388; 530/395; 530/806; 530/808; 530/828; 435/172.2; 435/240.27
[58] Field of Search ........... 424/85; 435/240.2, 68, 435/240.27, 172.2, 70; 530/387; 935/100, 102-104, 107, 108, 110

[56] References Cited

U.S. PATENT DOCUMENTS

| | | | |
|---|---|---|---|
| Re. 32,833 | 1/1989 | Greene et al. | 435/240.27 |
| 4,172,124 | 10/1979 | Koprowski et al. | 530/387 |
| 4,196,265 | 4/1980 | Koprowski | 435/2 |
| 4,331,647 | 5/1982 | Goldenberg | 424/1.1 |
| 4,446,128 | 5/1984 | Baschang | 424/88 |
| 4,455,296 | 6/1984 | Hansen | 424/87 |
| 4,464,465 | 8/1984 | Lostrum | 435/68 |
| 4,489,710 | 12/1984 | Spitler | 424/85 |
| 4,731,237 | 3/1988 | Reagan et al. | 435/240.27 |
| 4,816,249 | 3/1989 | Levy et al. | 424/85.8 |

FOREIGN PATENT DOCUMENTS

| | | |
|---|---|---|
| 0868099 | 6/1977 | Belgium . |
| 900023A | 10/1984 | Belgium . |
| 082789A | 6/1983 | European Pat. Off. . |
| 106615A | 4/1984 | European Pat. Off. . |
| 0110706A2 | 6/1984 | European Pat. Off. . |
| 0113431A2 | 7/1984 | European Pat. Off. . |
| 119629A | 9/1984 | European Pat. Off. . |
| 139389A | 5/1985 | European Pat. Off. . |
| 0142345A2 | 5/1985 | European Pat. Off. . |
| 3145007 | 5/1983 | Fed. Rep. of Germany . |
| 2819110 | 5/1985 | Fed. Rep. of Germany . |
| WO8402848 | 8/1984 | PCT Int'l Appl. . |
| 8404327A | 11/1984 | PCT Int'l Appl. . |
| 8502909 | 7/1985 | PCT Int'l Appl. . |

Primary Examiner—Robert J. Warden
Assistant Examiner—Jeff Kushan

[57] ABSTRACT

A method of inducing an immunological response to solid tumors is provided wherein anti-idiotype antibodies presenting an internal image of a tumor or antigen are administered to a patient. Monoclonal anti-idiotype antibodies and immortal B lymphocytes that produce them are also provided.

17 Claims, No Drawings

INDUCTION OF ANTIBODY RESPONSE TO SOLID TUMORS WITH ANTI-IDIOTYPE ANTIBODIES

This application is a continuation of application Ser. No. 549,505, filed Nov. 7, 1983, now abandoned.

TECHNICAL FIELD

The present invention is directed to the induction of immunological responses to tumors. More specifically, the present invention is directed to the use of anti-idiotype antibodies to induce an immunological response to tumors, as well as the antibodies and cell lines that produce them.

BACKGROUND OF THE INVENTION

The sequence of amino acids in the variable regions of both heavy ($V_H$) and light ($V_L$) chains of immunoglobulin (Ig) produces a conformation in the antigen binding site (i.e., parotope) allowing interaction of that antibody with a specific antigen. Injection of Ig into a heterologous host animal will give rise to anti-xenotypic (specific for species), anti-isotypic (specific for Ig class), and anti-idiotypic (specific for antibody variable region) antibodies. Two functional classes of anti-idiotypic antibodies can exist, one of which reacts with the parotope, and another which reacts with the $V_H$ and/or $V_L$ framework (framework determinants). See generally, Geha, (1981) N. Engl. J. Med. 305:25-28; Jerne, (1974) Ann. Immunol. (Paris) 125C: 373-389.

SUMMARY OF THE INVENTION

It is an object of the present invention to provide a method of inducing an immunological response in a patient to a solid tumor.

It is also an object of the present invention to employ anti-idiotype antibodies to produce an immunological response to solid tumors.

Another object of the present invention is to provide an alternative to the treatment of tumors with anti-tumor antibodies.

A further object of the present invention is to provide a method of treating solid tumors that takes advantage of the idiotypic network.

Yet another object of the present invention is to provide monoclonal anti-idiotype antibodies, and immortal B lymphocyte sources for such antibodies, that are useful in the induction of immunological responses to solid tumors.

These and other objects of the present invention are achieved by one or more of the following embodiments.

In one embodiment, the present invention provides a method of inducing an immunological response to a solid tumor comprising: (a) providing an anti-idiotype antibody, an epitope identified by said anti-idiotype antibody being the parotope of an anti-tumor antibody; and (b) stimulating in a human the production of anti-(anti-idiotype) antibody that identifies an epitope on a tumor cell by administering said anti-idiotype antibody to said human.

The present invention also provides polyclonal anti-idiotype antibodies, an epitope identified by said anti-idiotype antibodies being the parotope of an anti-tumor antibody, substantially free of anti-isotype antibodies.

In another embodiment, the present invention provides an immortal B lymphocyte that produces an anti-idiotype antibody, an epitope identified by said anti-idiotype antibody being the parotope of an anti-tumor antibody. The present invention also provides the monoclonal antibodies produced by the above immortal B lymphocyte substantially free of other antibodies.

In a further embodiment, the present invention provides a method of including an immunological response to a solid gastrointestinal tumor comprising: (a) providing an anti-idiotype antibody that identifies an epitope in the variable region of an anti-gastrointestinal tumor antibody; and (b) administering said anti-idiotype antibody to a human, said human being thereby stimulated to produce anti-(anti-idiotype) antibody that identifies an epitope on a gastrointestinal tumor cell.

DETAILED DESCRIPTION OF THE INVENTION

The present invention provides a unique approach to cancer therapy. Traditional approaches have employed administering anti-tumor antibodies (i.e., antibodies that identify an epitope on a solid tumor cell) to patients in an effort to destroy the tumor. Applicants, however, have discovered that an immunological response to a patient's own solid tumors can be induced with an antibody that is anti-idiotypic to an antibody that recognizes a tumor antigen. The induction of this immunological response has utility as a therapeutic, and possible preventative, treatment.

Although applicants do not wish to be bound by any particular theory of operability, it is believed that the observed immunological response achieved by the present invention is attributable to an interaction between the anti-idiotype antibody molecules and the human patient's immune system. The idiotypic (i.e., variable) region of the anti-idiotype antibody molecule contains antigenic determinants (i.e., epitopes) seen as an antigen by the patient. This induces the production of anti-(anti-idiotype) antibodies by the patient. Within this set of anti-(anti-idiotype) antibodies are those that are directly complimentary to the parotope of the anti-idiotype antibody. It is further believed that the parotope of the anti-idiotype antibody presents an "internal" image of the tumor cell epitope identified (i.e., selectively bound) by the idiotype antibody and, therefore, the anti-(anti-idiotype) antibodies will also bind the tumor antigen. In effect, the present method induces a immunological response to the solid tumor by presenting an antigen (the parotope of the anti-idiotype antibody) which is essentially indistinguishable from the tumor antigen to a portion of the patient's resulting antibodies.

Surprisingly, the above method is an effective procedure for controlling tumor growth. Furthermore, it has several advantages over the more traditional approach of limiting tumor growth with anti-tumor antibodies. First, much less foreign antibody need be administered to a patient. Second, the patient's anti-idiotype response is beneficial rather than detrimental to the intended effect. Third, the patient's own antibodies are the anti-tumor antibodies, thus eliminating the necessity of repeated administration of exogenous anti-tumor antibodies. Other advantages will be readily apparent to those of skill in the art.

The idiotype of an antibody is defined by individually distinctive antigenic determinants in the variable or idiotypic region of the antibody molecule. A portion of these idiotypic determinants will be on or closely associated with the parotope of the antibody, while others will be in the framework of the variable region. While each antibody has its own idiotype, particular antibodies will be referred to below by the following terms. "Idiotype antibody" or "Id Ab" refers to an anti-tumor antibody (i.e, the epitope identified by the idiotype antibody is on a cell of a solid tumor. "Anti-idiotype antibody" or "anti-Id Ab" refers to an antibody which identifies an epitope in the variable region of an idiotype antibody. A portion of such antibodies will identify an epitope that is the parotope antibody, thus presenting an "internal" image of the epitope identified by the idiotype antibody on the tumor cell. "Anti-(anti-idiotype) antibody" or "anti-(anti-Id) Ab" is an antibody that identifies an epitope in the variable region of the anti-idiotype antibody. A portion of the anti-(anti-idiotype) antibodies will identify an epitope that corresponds to (i) the parotope of the anti-idiotype antibody, and (ii) an epitope on a tumor cell.

As stated below, the method of the present invention contemplates administering anti-idiotype antibody to a host. The anti-idiotype antibody is administered to the host in any physiologically suitable carrier (e.g., sterile, pyrogen-free physiological saline), the formulations of which are within the skill of the art. The selection of carrier is not critical and the antibody can be administered by any method that introduces the antibody into the circulatory system (e.g., intravenous, intramuscular or subcutaneous injection).

The amount of antibody administered to a host can vary widely dependent, for example, upon the particular antibody employed and the patient inoculated. It is only necessary that sufficient anti-idiotype antibody be administered to stimulate the production of anti-(anti-idiotype) antibodies by the patient's immune system. The amounts of antibody employed, need not be very great because only very small amounts are necessary to induce an immunological response. In many cases, a dosage of antibody within the range of a few micrograms to a few milligrams should be sufficient, (e.g., about 50–200 μg to about 1–5 mg). The determination of an appropriate dosage is readily within the skill of the art.

In one embodiment, the present invention contemplates administering a formulation containing anti-idiotype antibody to a human patient to produce an immunological response to a solid tumor (i.e., a solid mass of malignant cells such as produced by carcinomas, sarcomas, melanomas etc., as opposed to disperse, circulating malignant cells such as leukemias). In a preferred embodiment, the tumor is a gastrointestinal tumor. As defined above, a subclass of the anti-idiotype antibody selectively binds to (i.e., identifies) the parotope of an anti-tumor antibody (the idiotype antibody). This subclass of anti-idiotype antibodies, which present internal images of the tumor antigen, can be distinguished from anti-idiotype antibodies that recognize framework determinants in the variable region of the idiotype antibody by any of several methods. One method of identifying the desired anti-idiotype antibodies is a competitive binding assay between the tumor antigen )or hapten if available), the idiotype antibody and the anti-idiotype antibody. If the antigen blocks binding of the anti-idiotype antibody to the idiotype antibody, the epitope identified by the anti-idiotype antibody is closely associated with the idiotype antibody's parotope. Another test is to determine if anti-sera to the anti-idiotype antibody is also anti-tumor. These and other methods of identifying the appropriate anti-idiotype antibody are within the skill of the art. In the formulation administered to a patient, the inclusion of anti-idiotype antibodies directed to framework determinants along with the subclass directed to the idiotype antibody's parotope is acceptable. It is only necessary that the formulation contain the subclass directed to the idiotype antibody's parotope.

The preferred anti-idiotype antibody is a human antibody to minimize immunological response to the constant region to the antibody molecule. However, since relatively small doses of anti-idiotype antibody are required in the present invention, heterologous antibody can be employed (e.g., mouse, rat, goat, rabbit, etc.). In the absence on any serious reaction to heterologous anti-idiotype antibody, however, such antibody may be preferred due to ease and cost of preparation. Furthermore, polyclonal anti-idiotype antibodies can be employed as well as monoclonal anti-idiotype antibodies.

Polyclonal anti-idiotype antibody can be prepared by conventional methods known in the art. For example, polyclonal anti-Id Ab can be produced by immunizing an animal with a monoclonal anti-tumor antibody (i.e., Id Ab). The immunized animal will produce anti-Id Ab. A subclass of this anti-idiotype antibody in the anti-sera will identify an epitope that is the parotope of the anti-tumor antibody. Anti-sera collected from the animal can be purified, for example, by sequential absorption with (i) an immobilized antibody of the same isotype as the monoclonal Id Ab, but different idiotype, to remove anti-isotypic antibodies from the anti-sera, and (ii) the immobilized monoclonal Id Ab to remove the anti-Id Ab, a subclass of which will present internal images of the tumor antigen. The anti-Id Ab can then be eluted from the bound monoclonal anti-tumor antibody to provide a solution substantially free of anti-isotype antibodies. This solution can then be tested for the presence of anti-Id Ab that identifies the parotope of the Id Ab.

Monoclonal anti-idiotype antibodies substantially free of other antibodies can be isolated from the supernatant of substantially pure cultures of immortal B lymphocytes. The term "immortal B lymphocyte" encompasses any relatively stable, continuous antibody-producing cell that can be maintained in culture for several months (preferably indefinitely), such as hybridomas (somatic cell hybrids of normal and malignant lymphocytes) and normal lymphocytes transformed by virus (e.g., Epstein-Barr virus) or oncogenic DNA. The production of immortal B lymphocytes from normal B lymphocytes that produce anti-isotype antibody is within the skill of the art. See, e.g., *Monoclonal Antibodies* (R. H. Kennett, T. J. McKearn & K. B. Bechtol 1980); M. Schreier et al., *Hybridoma Techniques* (Cold Spring Harbor Laboratory 1980); *Monoclonal Antibodies and T-Cell Hybridomas* (G. J. Hammerling, U. Hammerling & J. F. Kearney 1981); Kozbor et al., (1982) *Proc. Natl. Acad. Sci. U.S.A.* 79:6651–6655; Jonak et al., (1983) *Hybridoma* 2:124; *Monoclonal Antibodies and Functional Cell Lines* (R. H. Kennett, K. B. Bechtol & T. J. McKearn 1983); Kozbor et al., (1983) *Immunology Today* 4: 72–79.

Normal B lymphocytes producing anti-Id Ab and suitable for the production of an immortal B lymphocyte can be provided by various methods within the skill of the art. For example, an animal, such as a rat or mouse, can be immunized with a monoclonal anti-tumor antibody and B lymphocytes producing anti-Id Ab recovered from the animal's spleen. Human B lymphocytes producing anti-Id Ab can be obtained by immunizing a patient with monoclonal anti-tumor antibody, collecting peripheral blood lymphocytes from the patient, and then inducing in vitro the growth of B lymphocytes producing anti-Id Ab by stimulating the culture with the monoclonal anti-tumor antibody. See, e.g., DeFreitas et al., (1982) *Proc. Natl. Acad. Sci. U.S.A.* 79:6646–6650. The animal or human B lymphocytes producing anti-Id Ab can thus be recovered and immortalized by those of skill in the art. Of course it is understood that those lymphocytes producing anti-Id Ab that present internal images of the tumor cell antigen should be distinguished from B lymphocytes producing anti-Id Ab directed to framework determinants in the idiotypic region.

The method of the present invention can also be practiced in conjunction with other methods of inducing immunological responses to tumors such as the use of viral oncolysate vaccines as described in U.S. Pat. No. 4,108,983.

The following examples are illustrative of the present invention and are not intended to limit its scope.

MONOCLONAL IDIOTYPE ANTIBODIES

The following experiments employed mouse monoclonal antibodies 17-1A, C$_4$2032 and C$_4$1472, which bind to human gastrointestinal cancer cells, and are described in Herlyn et al., (1979) *Proc. Natl. Acad. Sci. U.S.A.* 76: 1438–1442 and Koprowski, "Monoclonal Antibodies In Vivo," in *Monoclonal Antibodies in Cancer: Proceedings of the Fourth Armand Hammer Cancer Symposium* (B. Boss, R. Langman, I. Trowbridge & Dulbecco 1983). Monoclonal antibody (MAb) C$_4$2032 has specificity for colorectal carcinoma (CRC)-associated antigen(s) of M$_r$ 180, 160, 50 and 40 K. MAb C$_4$1472 (IgG2a) has specificity for CRC-associated antigen M$_r$ 50 K. The MAb A5C3 against hepatitis virus was also employed and is described in Wands et al., (1981) *Proc. Natl. Acad. Sci. U.S.A.* 78: 1214–1218. MAb's 17-1A (IgG2A, kappa light chain) and C$_4$2032 (IgG2a kappa light chain) were purified from ascites obtained hybridoma-bearing mice by affinity chromotography on protein A-sepharose column (Pharmacia, Piscataway, N.J.) as described by Ey et al., (1978) *Immunochemistry* 15: 429–436.

PATIENTS

All patients had metastatic or recurrent gastrointestinal adenocarcinoma and were injected systematically with one dose of a purified sterile, pyrogen-free preparation of MAb 17-1A concentrated from ascites fluid of Balb/c mice per the method disclosed in Sears et al., (1982) *Lancet* 762–765. Of nine patients who received 192 mg or less of MAb 17-1A seven developed anti-mouse globulin antibodies. Of the 20 patients who received 200–1000 mg of monoclonal antibody, three developed anti-mouse globulin antibodies. Sera of three patients of the first group who developed anti-mouse globulin molecules (patient Nos. 07, 08 and 09) and of two patients of the second group (Nos. 14 and 23), were either screened or processed for isolation of anti-idiotype antibodies. Sera used for isolation of anti-idiotype antibodies from subject Nos. 07, 08 and 23 were obtained at the time when all three showed the highest concentration of anti-mouse globulin antibodies. Patient No. 08 received a second injection of 130 mg of monoclonal antibody 20 months after the first injection, and serum obtained after this second injection was used in a screening test for the presense of anti-idiotype antibody.

PREPARATION OF POLYCLONAL ANTI-IDIOTYPE ANTIBODIES

New Zealand white rabbits were injected subcutaneously at multiple sites with 300 μg purified MAb 17-1A emulsified in Freund's complete adjuvant and, 30 days later, boosted intramuscularly with 100 μg of the monoclonal antibody. Sera was collected on day 10 of the secondary response.

Anti-sera was absorbed on immobilized MAb C$_4$2032 and MAb 17-1A. The purified monoclonal antibodies (30 mg each) were coupled to 2 ml of Affi-Gel 10 (Bio-Rad Laboratories, Richmond, Calif.). The anti-sera was then sequentially absorbed on MAb C$_4$2032 and MAb 17-1A immunoabsorbents to remove anti-isotypic and anti-idiotypic antibodies, respectively. Absorbed antibodies were eluted with 0.1M glycine buffer (pH 2.8), immediately neutralized with phosphate buffer, dialyzed against phosphate-buffered saline, and protein quantitated by absorptivity at 280 nm ($E^{1\%}_{280} = 14$).

Anti-sera obtained from patients after one injection of MAb 17-1A was also obtained and purified as described above. Sera from subject No. 23, received 750 mg of MAb 17-1A, and from subjects No. 08 and 07, who received 133 and 125 mg of MAb 17-1A, respectively, were collected at various times after the first injection of antibody. Samples shown by radioimmunoassay analysis to contain antimurine IgG antibody were sequentially absorbed on MAb C$_4$2032 and MAb 17-1A immunoabsorbents to remove anti-isotypic and anti-idiotypic antibodies, respectively, as described above. The anti-idiotype antibody isolated from the sera was shown to be human immunoglobulins by binding to $^{125}$I-labeled anti-human F(ab')$_2$ fragments. The yield of anti-idiotype protein from serum samples varied: 13 μg/ml from No. 08; 8.9 μg/ml from No. 07; and 43 μg/ml from No. 23. The largest amount was obtained from No. 23 serum which also showed the highest levels of anti-mouse globulin antibodies.

SCREENING SERA FOR PRESENCE OF ANTI-IDIOTYPE ANTIBODIES

To screen serum samples for the presense of anti-idiotype antibody, a competition assay was performed using the rabbit-anti-idiotype antibody and four human sera pre-incubated with $^{125}$I-labeled MAb 17-1A.

Polystyrene beads of ¼-inch (6.35 mm) size (Precision Plastic Ball Co., Chicago, Ill.) were washed three times with 95% ethanol. The air-dried beads were incubated with a dilution of either rabbit or human anti-idiotype antibody in 0.02M sodium tetraborate, pH 8.2. After overnight incubation at 4° C. with gentle shaking, the beads were washed three times with phosphate-buffered saline and then incubated for at least three hours at room temperature with phosphate-buffered saline containing 2% bovine serum albumin and 0.04% NaN$_3$. The beads were then exposed to $^{125}$I-labeled MAb 17-1A as the reference idiotype that had been preincubated with the potential source of human anti-idiotype antibody, i.e., human sera was diluted to 25% concentration in phosphate-buffered saline without Ca$^{++}$ and Mg$^{++}$ and supplemented with 2% bovine serum albumin and 0.04% NaN$_3$. After an additional overnight incubation, the beads were washed and the radioactivity bound was measured in a gamma counter.

Three of the sera obtained after one injection with monoclonal antibody, Nos. (23, 09, and 14) showed inhibition of binding of MAb 17-1A that was higher than that of pre-monoclonal antibody injection samples. Binding inhibition values obtained for post-monoclonal antibody serum of patient No. 14 were low as compared to the other two sera, but higher than that for the pre-monoclonal antibody exposure serum of the same subject. Inhibition values for serum obtained from patient No. 08 seven days after he received a second injection of monoclonal antibody were already high.

COMPETITION ASSAY FOR DETECTION OF ANTI-IDIOTYPE

A competition assay was conducted in a manner similar to that described above to determine the binding of isolated anti-idiotype antibodies to MAb 17-1A, as well as to monoclonal antibodies $C_{42032}$, $C_{41472}$ and A5C3.

The results indicated that the binding of anti-idiotype antibodies from three sera (Nos. 08, 07 and 23) to MAb 17-1A was significantly higher than to the three other monoclonal antibodies, two of which ($C_{42032}$ and $C_{41472}$) also detect antigenic sites on colorectal carcinoma cells. These sites, however, are different from the sites recognized by MAb 17-1A. The immunoglobulin isolated from the sera of all three subjects prior to exposure to MAb 17-1A was concentrated to approximately 2.5 μg/ml and coupled to polystyrene beads. These preparations, however, did not bind any of the monoclonal antibodies tested, indicating the absense of anti-idiotype antibodies in pre-exposure serum.

CROSS-REACTIVITY BETWEEN ANTI-IDIOTYPE ANTIBODIES

A competition assay was conducted to determine whether there was cross-reactivity among the human anti-Id sera.

Results of the competition assay, shown below, indicates significant cross-reactivity between anti-idiotype sera of patients No. 07 and 23, and slightly less (but still significant) cross-reactivity between the anti-idiotype sera of patients Nos. 08 and 23. Similar cross-reactivity was found between the anti-idiotype sera of patient No. 07 and post-monoclonal antibody serum obtained from patient No. 08 (results not shown). These results indicate that the anti-idiotype antibodies produced by different patients are directed against the same antigenic site.

| 1st Antibody | 2nd Antibody Serum of: | cmp bound | % of Inhibition of 17-1A MAb Binding |
|---|---|---|---|
| | None | 4297 | |
| anti-Id 23 | 07 Pre | 4595 | 0 |
| | Post | 1231 | 71 |
| | 08 Pre | 4097 | 5 |
| | Post | 2585 | 40 |

EPITOPE DETECTED BY ANTI-IDIOTYPE ANTIBODY

Hapten inhibition of binding of human anti-idiotype antibodies to MAb 17-1A was performed to show that the anti-idiotype antibodies were directed to the parotope of the idiotype antibody.

A 3M KCl extract of SW 1222 cells, a cell line derived from colorectal cancer, was prepared as described in Herlyn et al., (1982) *J. Clin. Immunol.* 2: 135–140. The preparation bound MAb 17-1A, indicating that the material contained the antigen in its soluble form. $^{125}$I-labeled MAb 17-1A was incubated with the CRC cell extract and with a 3M KCl extract of melanoma cells which do not bind MAb 17-1A. The antibody-antigen mixtures were then added to beads coated with anti-idiotype antibody obtained from patient No. 23 and the binding compared to the binding of the radiolabeled monoclonal antibody alone. These experiments were performed with non-saturating amounts of iodinated monoclonal antibody in order to detect changes in binding with small amounts of competitive haptens. For control purposes, the iodinated MAb 17-1A was mixed with an extract from melanoma cells that was known not to bind MAb 17-1A. The CRC cell extracts in concentrations of 0.1 or 0.5 mg/ml were found to inhibit the binding of the anti-idiotype antibody from patient No. 23 to iodinated MAb 17-1A by 39% and 68%, respectively. The extract from melanomia cells in concentrations up to 0.5 mg/ml did not significantly affect the monoclonal antibody binding.

This hapten inhibition of the binding reaction indicates the presence of an "internal image" of the CRC epitope on the anti-idiotype antibody. This is also support by the fact that the finding that the extract of CRC cells did not bind to the anti-idiotype antibodies but did bind, as expected, to MAb 17-1A.

PRODUCTION OF ANTI-IDIOTYPE AND ANTI-(ANTI-IDIOTYPE) ANTIBODIES BY HUMAN B LYMPHOCYTES

Buffy coat cells were obtained from patient Nos. 08 and 23, twenty and five months, respectively, after injection with MAb 17-1A. The cells were stimulated with 10 ng/ml F(ab')$_2$ fragments of 17-1A in vitro as described in DeFreitas et al., (1982), *Proc. Natl. Acad. Sci. U.S.A.* 79: 6646–6650. During the following seven days, aliquots of cells were separated into T and B cell populations by rosetting with sheep erythrocytes treated with 2-amino ethylisouronium bromide. See, Pellogrino et al., (1975) *Clin. Immunol. & Immunopathol.* 3: 324–333. Both cell populations were stained with F(ab')$_2$ fragments of 17-1A or anti-influenza monoclonal antibody, and goat anti-mouse Ig-FITC. The cell populations were then subsequently analyzed in a cytofluorograph. In addition, peripheral blood mononuclear cells from the same patient were stimulated with F(ab')$_2$ fragments of 17-1A or anti-influenza monoclonal antibodies for nine days in a modified Mishell-Dutton culture for specific human Ig production as described in DeFreitas et al., supra. Supernatants from these cultures were assayed in a solid-phase enzyme-linked immunoabsorbent assay for specific human IgG (KPL Laboratories, Gaithersburg, Md.).

The percentage of lymphocytes that initially bound 17-1A F(ab')$_2$ of patent No. 08 was 1.2%, and of patient No. 23 was 0.2%. During seven days in culture with MAb 17-1A, the percentage of lymphocytes of patent No. 23 that specifically bound 17-1A F(ab')$_2$ increased from 0.2 to 13%. All the 17-1A binding cells were present in the B cell population. In addition, after nine days, human anti-MAb 17-1A IgG was detected. Incubation of lymphocytes from the same patient with anti-influenza monoclonal antibody under identical conditions produce no detactable human I$_g$ to either MAb 17-1A or anti-influenza monoclonal antibodies.

In another experiment, human B lymphocytes were stimulated to produce anti-(anti-idiotype) antibody. B lymphocytes were collected and stimulated in vitro as described above, except that the cells were stimulated with autologous anti-idiotype antibody rather than idiotype antibody. Anti-(anti-idiotype) antibodies were produced by stimulated B lymphocytes and these anti-(anti-Id) Ab were shown to identify as epitope on CRC cell extract and on whole cells. Thus, the human immune system will produce anti-tumor antibodies in response to stimulation with anti-idiotype antibodies.

IMMORTAL B LYMPHOCYTES PRODUCING ANTI-IDIOTYPE ANTIBODY

Various methods of producing immortal B lymphocytes secreting monoclonal antibodies are known in the art. See Kozbor et al., (1983) *Immunology Today* 4: 72-79. Human B lymphocytes secreting anti-(anti-idiotype) antibody, obtained from peripheral blood lymphocytes as described above, can be immortalized, therefore, by one of skill in the art.

One method that can be readily employed is immortalization with Epstein-Barr virus (EBV). In this method, the normal lymphocytes described above are infected with EBV in vitro and immortal cell lines then establish, for example, by limiting dilution on a feeder layer. See, e.g., Kozbor, et al., (1983), supra, and references 51-60 cited therein.

Another approach is to fuse either the above described anti-Id Ab secreting lymphocytes or an EBV-transformed lymphocyte with a human plasmacytoma or lymphoblastoid fusion partner. For example, an EBV-transformed B lymphocyte secreting anti-Id Ab can be fused with, for example, the human lymphoblastoid cell line KR-4. The desired hybridomas would then be selected for in hypoxanthine-aminopterin-thymidine medium containing ouabain, which eliminates the parental cells. Hybridomas are tested for specific antibody production. Positive hybrids are then cloned, recloned and then propagated in bulk culture or in the peritoneal cavity of an immune-suppressed mammal (e.g., nude mouse). See, e.g., Kozbor et al., (1982) *Proc. Natl. Acade. Sci. USA* 79: 6651-6655.

The above examples were presented for illustrative purposes only and are not intended to limit the invention which is defined solely by the claims.

We claim:

1. A method of stimulating production of antibodies which bind to an epitope on a solid tumor cell comprising:
administering a monoclonal anti-idiotypic antibody which bears an internal image of an epitope present on a solid tumor cell to a human in an amount sufficient to stimulate the production of an anti-anti-idiotypic antibodies which immunoreact with said solid tumor cell epitope,
wherein said monoclonal anti-idiotypic antibody immunoreacts through its paratope with a monoclonal antibody specific for said solid tumor cell epitope.

2. The method of claim 1 wherein said anti-idiotype antibody is a human antibody.

3. The method of claim 1 wherein said anti-idiotype antibody is selected from the group consisting of mouse and rat antibodies.

4. An immortalized B lymphocyte that produces a monoclonal anti-idiotypic antibody which bears the internal image of an epitope present on a solid tumor cell, wherein said anti-idiotypic antibody
(a) immunoreacts with paratope of a monoclonal antibody specific for said solid tumor cell epitope; and
(b) will induce formation of anti-anti-iodiotypic antibodies specific for said solid tumor cell epitope upon administration to a human.

5. The immortalized B lymphocyte of claim 4 that is a human lymphocyte.

6. The immortalized B lymphocyte of claim 4 that is selected from the group consisting of mouse and rat lymphocytes.

7. The immortalized B lymphocyte of claim 4 that is a hybridoma.

8. The immortalized B lymphocyte of claim 5 that is a hybridoma.

9. The monoclonal antibodies produced by the immortal B lymphocyte of claim 4 substantially free of other antibodies.

10. The monoclonal antibodies produced by the immortal B lymphocyte of claim 5 substantially free of other antibodies.

11. The monoclonal antibodies produced by the immortal B lymphocyte of claim 6 substantially free of other antibodies.

12. The monoclonal antibodies produced by the immortal B lymphocyte of claim 7 substantially free of other antibodies.

13. The monoclonal antibodies produced by the immortal B lymphocyte of claim 8 substantially free of other antibodies.

14. A polyclonal antibody preparation comprising antibodies bearing the internal image of an epitope present on a solid tumor cell, wherein said anti-idiotypic antibodies
(a) immunoreact through their paratopes with the paratope of a monoclonal antibody specific for said solid tumor cell epitope; and
(b) induce formation of anti-anti-iodiotypic antibodies specific for said solid tumor cell epitope upon administration to a human;
and wherein said polyclonal antibody preparation is substantially free from anti-isotype antibodies and is produced by immunizing a mammalian host with a monoclonal antibody specific for said solid tumor cell epitope.

15. A method of stimulating production of antibodies which bind to an epitope on a solid gastrointestinal tumor comprising:
administering a monoclonal anti-idiotypic antibody which bears an internal image of an epitope present on a solid gastrointestinal tumor cell to a human in an amount sufficient to stimulate the production of an anti-anti-idiotypic antibodies which immunoreact with said solid gastrointestinal tumor cell epitope,
wherein said monoclonal anti-idiotypic antibody immunoreacts through its paratope with a monoclonal antibody specific for said solid gastrointestinal tumor cell epitope.

16. A method of stimulating production of antibodies which bind to an epitope on a solid tumor cell comprising:
administering the polyclonal antibody preparation of claim 14 to a human in an amount sufficient to stimulate the production of an anti-anti-idiotypic antibodies which immunoreact with said solid tumor cell epitope.

17. The method of claim 16 wherein said solid tumor cell is a gastrointestinal tumor cell.

* * * * *

UNITED STATES PATENT AND TRADEMARK OFFICE
CERTIFICATE OF CORRECTION

| | | |
|---|---|---|
| PATENT NO. : | 5,053,224 | Page 1 of 9 |
| DATED : | October 1, 1991 | |
| INVENTOR(S) : | Koprowski, et al. | |

It is certified that error appears in the above-identified patent and that said Letters Patent is hereby corrected as shown below:

TITLE PAGE:
REFERENCES CITED

After the heading "FOREIGN PATENT DOCUMENTS" and subsequent list of documents, please insert the heading —OTHER PUBLICATIONS— and insert the following prior art:

Binz, et al., Intl. J. Cancer, vol. 29(4), pp. 417-423 (1982), Bio. Abst. 75027544.

Bluestone, et al., Nature, vol. 291, pp. 233-235 (1981).

Bona, et al., J. Exp. Med., vol. 153, pp. 951-967 (1981).

Bona, et al., J. Exp. Med., vol. 156, pp. 986-999 (1982), Chemical Abstracts, vol. 97, 179920c (1982)

Cahan, et al., Proc. Natl. Acad. Sci. USA, vol. 79, 7629-7633 (1982).

Cazenave, Proc. Natl. Acad. Sci. USA, vol. 74(11), pp. 5122-5125 (1977).

Cerny, et al., J. Immunology, vol. 128(4), pp. 1885-1891 (1982).

UNITED STATES PATENT AND TRADEMARK OFFICE
CERTIFICATE OF CORRECTION

PATENT NO.   :   5,053,224
DATED        :   October 1, 1991
INVENTOR(S)  :   Koprowski, et al.

It is certified that error appears in the above-identified patent and that said Letters Patent is hereby corrected as shown below:

Eichman, Eur. J. of Immunol., vol. 4, pp. 296-302 (1974).

Eichman, et al., Eur. J. of Immunol., vol. 5, pp. 661-666 (1975).

Eichman, et al., J. Exp. Med., vol. 153, pp. 951-967 (1981).

Eichmann, et al., Springer Seminars in Immunopathology, vol. 6, pp. 7-32 (1983).

Eilat, et al. Proc. Natl. Acad. Sci. USA, vol. 79, pp. 3818-3822 (1982).

Evans, et al., Molecular Immunology, vol. 20, no. 10, pp. 1127-1131 (1983).

Forstrom, et al., Nature, vol. 303, pp. 627-629 (1983).

Geha, N. Engl. J. Med., vol. 305, pp. 25-28 (1981).

Goldman, et al., Springer Seminars in Immunopathology, vol. 6, pp. 33-49 (1983).

Greene, et al., Proc. Natl. Acad. Sci. USA, vol. 74(11), pp. 5118-5121 (1977).

UNITED STATES PATENT AND TRADEMARK OFFICE
CERTIFICATE OF CORRECTION

PATENT NO. : 5,053,224

DATED : October 1, 1991

INVENTOR(S) : Koprowski, et al.

It is certified that error appears in the above-identified patent and that said Letters Patent is hereby corrected as shown below:

Gheuens, et al., Infection and Immunity, vol. 34, pp. 200-207 (1981).

Haughton, et al., Journal of Immunology, vol. 121, no. 6, pp. 2358-2362 (1978).

Herlyn, et al., Proc. Natl Acad. Sci. USA, vol. 76, pp. 1438-1442 (1979).

Ionescu-Matiu, et al., Journal of Immunology, vol. 130, no. 4, pp. 1947-1952 (1983).

Jaffers, et al., Transplant Proc., vol. 15, pp. 646-648 (1983).

Jerne, et al., Euro. Mol. Biol. Organ, J., vol. 1(2), pp. 243-248 (1982) Bio. Abst 75010677.

Ju, et al., Journal of Immunology, Chemical Abstracts, vol. 100, 207644c, 1984.

Kauffman, et al., Journal of Immunology, vol. 131, pp. 2539-2541 (1983).

UNITED STATES PATENT AND TRADEMARK OFFICE
CERTIFICATE OF CORRECTION

PATENT NO. : 5,053,224

DATED : October 1, 1991

INVENTOR(S) : Koprowski, et al.

It is certified that error appears in the above-identified patent and that said Letters Patent is hereby corrected as shown below:

Kazdin, et al., Molecular Immunology, vol. 20(8), pp. 819-826 (1983) Biol Abst. 77-35483.

Kelsoe, et al., Immunol. Rev., vol. 52, pp. 75-88 (1980).

Kennedy, et al., Journal of Virology, vol. 46, no. 2, pp. 653-655 (1983).

Kennedy, Mod. Appr. Vacc., Chemical Abstracts, vol. 101, 108793d (1984).

Kim, et al., Journal of Immunology, vol. 131, no. 1, pp. 13-15 (1983).

Koprowski, et al., Proc. Natl. Acad. Sci. USA, vol. 81, pp. 216-219 (1984).

Kozbor, et al., Proc. Natl. Acad. Sci. USA, vol. 76, pp. 6651-66 (1982).

Legrain, et al., Eur. J. Immunol., vol. 11, pp. 678-685 (1981).

Levy, et al., Fed. Proc., vol. 42, pp. 2650-2656 (1983).

Lipinski, et al., Journal of Immunology, vol. 129, pp. 2301-2304 (1982).

Magnani, et al., J. Biological Chemistry, vol. 257, pp. 14365-9 (1982).

UNITED STATES PATENT AND TRADEMARK OFFICE
CERTIFICATE OF CORRECTION

PATENT NO. : 5,053,224

DATED : October 1, 1991

INVENTOR(S) : Koprowski, et al.

It is certified that error appears in the above-identified patent and that said Letters Patent is hereby corrected as shown below:

Metzger, et al., J. Exp. Med., Chemical Abstracts, vol. 95, 166973f (1981).

Metzger, European Journal of Immunology, vol. 14, pp. 304-308 (1984).

Miller, et al. N. Engl. J. Med. vol. 306, pp. 517-522 (1982).

Morahan, Aust. J. Exp. Biol. Med. Sci., vol. 60, (pt 4), pp. 369-382 (1982).

Morahan, J. Imm. Met., vol. 57, pp. 165-170 (1983).

Nepom, et al., J. Exp. Med., vol. 155, pp. 155-167 (1982).

Nepom, et al., Proc. Natl. Acad. Sci. USA, vol. 81, pp. 2864-2867 (1984).

Nisonoff, et al., Clinical Immunology and Immunopathology, vol. 21, pp. 397-406 (1981).

Noseworthy, et al., Journal of Immunology, vol. 131, no. 5, pp. 2533-2538 (1983).

UNITED STATES PATENT AND TRADEMARK OFFICE
CERTIFICATE OF CORRECTION

PATENT NO. : 5,053,224
DATED : October 1, 1991
INVENTOR(S) : Koprowski, et al.

Page 6 of 9

It is certified that error appears in the above-identified patent and that said Letters Patent is hereby corrected as shown below:

Nowinski, et al., Science, vol. 210, pp. 537-539 (1980), Bio. Abst. 71066926.

Reagan, et al., Journal of Virology, vol. 48, pp. 660-666, (1983).

Reth, et al., Eur. J. Immunol., vol. 99, p. 1004 (1979).

Reth, et al., Nature, vol. 290, pp. 257-259 (1981).

Ritz, et al., Blood, vol. 58, pp. 141-152 (1981).

Rodkey, Microbiological Review, vol. 44, pp. 631-659 (1980).

Roitt, et al., Springer Seminars in Immunopathology, vol. 6, pp. 51-66 (1983).

Rubinstein, et al., J. Exp. Med., vol. 158(4), pp. 1129-1144 (1983).

Sacks, et al., J. Exp. Med., vol. 155, pp. 1108-1119 (1982).

Sacks, et al., Springer Seminars in Immunopathology, vol. 6, pp. 79-97 (1983).

UNITED STATES PATENT AND TRADEMARK OFFICE
CERTIFICATE OF CORRECTION

PATENT NO. : 5,053,224

DATED : October 1, 1991

INVENTOR(S) : Koprowski, et al.

It is certified that error appears in the above-identified patent and that said Letters Patent is hereby corrected as shown below:

Schlom, et al., Proc. Natl Acad. Sci. USA, vol. 77(11), pp. 6841-6815 (1980).

Schreiber, et al., J. Natl Cancer Institute, vol. 60, p. 225 (1978).

Sege, et al., Proc. Natl Acad. Sci. USA, vol. 75, pp. 2443-2447 (1978).

Sher, et al., Journal of Immunology, vol. 109, pp. 176-178 (1972).

Steinitz, et al., Immunobiol., vol. 156, pp. 41-47 (1979).

Steinitz, et al., Journal of Immunology, vol. 141, no. 10, pp. 3516-3522 (1988).

Stevenson, et al., Springer Seminars in Immunolopathology, vol. 6, pp. 99-115 (1983).

Strosberg, et al., Springer Seminars in Immunopathology, vol. 6, pp. 67-78 (1983).

Thielemans, et al., Journal of Immunology, vol. 133, no. 1, pp. 495-501 (1984).

UNITED STATES PATENT AND TRADEMARK OFFICE
CERTIFICATE OF CORRECTION

PATENT NO. : 5,053,224

DATED : October 1, 1991

INVENTOR(S) : Koprowski, et al.

It is certified that error appears in the above-identified patent and that said Letters Patent is hereby corrected as shown below:

Urbain, et al., Proc. Natl. Acad. Sci. USA., vol. 74(11), pp. 5126-5130 (1977).

Urbain, Springer Seminars in Immunopathology, vol. 6, pp. 1-5 (1983).

Urban, et al., Fed. Proc. 69th Meeting, Abst. 4588 (1980).

Viale, et al., "Idiotypic Replica of an Anti-human Tumor-associated Antigen Monoclonal Antibody," Journal of Immunology, vol. 143, no. 12, Dec. 15, 1989.

Wikler, et al., J. Exp. Med., vol. 150, pp. 184-195 (1979).

Weaver, et al., Prot. Conf. Immunol. (1981), Chemical Abstracts, vol. 100, 83892z (1984).

UNITED STATES PATENT AND TRADEMARK OFFICE
CERTIFICATE OF CORRECTION

PATENT NO. : 5,053,224
DATED : October 1, 1991
INVENTOR(S) : Koprowski, et al

It is certified that error appears in the above-indentified patent and that said Letters Patent is hereby corrected as shown below:

Yeh, et al., International Journal of Cancer, vol. 29, pp. 269-275 (1982)

Nelson, et al., Fed. Proc. (4/10/83), "Modulation of Tumor Immunity by a Monoclonal Auto-Anti-Idiotypic Antibody Which Binds a Monoclonal T Cell Suppressor Factor," Immune Response to Tumors, Abst. 4627, p. 1082.

Signed and Sealed this

Twelfth Day of July, 1994

BRUCE LEHMAN

Attesting Officer    Commissioner of Patents and Trademarks